(12) United States Patent
Matsunaga et al.

(10) Patent No.: US 10,191,010 B2
(45) Date of Patent: Jan. 29, 2019

(54) TRANSFER MEMBRANE RETAINING JIG AND SEPARATION-TRANSFER DEVICE

(71) Applicant: Sharp Life Science Corporation, Kobe, Hyogo (JP)

(72) Inventors: Takateru Matsunaga, Sakai (JP); Hideki Kinoshita, Sakai (JP)

(73) Assignee: SHARP LIFE SCIENCE CORPORATION, Kobe, Hyogo (JP)

( * ) Notice: Subject to any disclaimer, the term of this patent is extended or adjusted under 35 U.S.C. 154(b) by 0 days.

(21) Appl. No.: 15/303,548

(22) PCT Filed: Dec. 7, 2015

(86) PCT No.: PCT/JP2015/084255
§ 371 (c)(1),
(2) Date: Oct. 12, 2016

(87) PCT Pub. No.: WO2016/136079
PCT Pub. Date: Sep. 1, 2016

(65) Prior Publication Data
US 2017/0350858 A1 Dec. 7, 2017

(30) Foreign Application Priority Data
Feb. 24, 2015 (JP) ................................. 2015-034587

(51) Int. Cl.
*G01N 27/453* (2006.01)
*G01N 27/447* (2006.01)

(52) U.S. Cl.
CPC ..... *G01N 27/44739* (2013.01); *G01N 27/447* (2013.01)

(58) Field of Classification Search
CPC ................................................ G01N 27/44739
See application file for complete search history.

(56) References Cited

U.S. PATENT DOCUMENTS

| | | | |
|---|---|---|---|
| 5,514,256 A * | 5/1996 | Douthart | G01N 27/44704 204/464 |
| 6,517,696 B1 | 2/2003 | Hayashizaki et al. | |
| 9,599,590 B2 | 3/2017 | Sabin et al. | |
| 2009/0127118 A1 | 5/2009 | Unuma et al. | |
| 2012/0322679 A1 | 12/2012 | Brown et al. | |
| 2013/0140183 A1 | 6/2013 | Tajima | |

FOREIGN PATENT DOCUMENTS

| | | |
|---|---|---|
| JP | 2007-292616 A | 11/2007 |
| JP | 2011-080842 A | 4/2011 |
| KR | 10-2006-0088516 A | 8/2006 |
| KR | 10-2012-0107105 A | 9/2012 |
| WO | 93/03359 A1 | 2/1993 |
| WO | 2011/162290 A1 | 12/2011 |
| WO | 2013/180642 A1 | 12/2013 |
| WO | 2014/059188 A1 | 4/2014 |
| WO | 2014/147395 A1 | 9/2014 |

* cited by examiner

*Primary Examiner* — Alexander S Noguerola
(74) *Attorney, Agent, or Firm* — ScienBiziP, P.C.

(57) ABSTRACT

A transfer-membrane retaining jig (2) that retains a transfer membrane (1) in a separation-transfer device (100) includes: a fixing part (20, 21) that fixes at least one end in a movement direction of the transfer membrane (1), in which the fixing part (20, 21) includes an elastic body (20*a*, 21*a*) that abuts the transfer membrane (1) from an opposite side to a dispensing part (50*a*), and a pressing member (20*b*, 21*b*) that presses the transfer membrane (1) against the elastic body (20*a*, 21*a*).

11 Claims, 5 Drawing Sheets

TRANSFER MEMBRANE RETAINING JIG AND SEPARATION-TRANSFER DEVICE

TECHNICAL FIELD

The present invention relates to electrophoresis, and in particular, relates to technology for separating an analyte by way of electrophoresis, and transferring the separated analyte to a transfer membrane.

BACKGROUND ART

A technology has been known for separating analyte by electrophoresis, dispensing the separated analyte from a dispensing part, and transferring the separated analyte to a transfer membrane by causing the transfer membrane to abut with the dispensing part and causing to move (hereinafter referred to as "direct blotting"). For example, Patent Document 1 discloses an example of a device for performing direct blotting.

Patent Document 1: Japanese Published Translation of PCT International Publication for Patent Applications "Japanese Unexamined Patent Application (Translation of PCT Publication), Publication No. 2007-292616 (published Nov. 8, 2007)"

DISCLOSURE OF THE INVENTION

Problems to be Solved by the Invention

When performing direct blotting, in order to favorably transfer the analyte dispensed from the dispensing part to the transfer membrane, it is very important to bring the transfer membrane into close contact with the dispensing part.

The present invention has been made by taking account of the above-mentioned problem, and has a main object of providing novel technology for bringing a transfer membrane into close contact with a dispensing part when performing direct blotting.

Means for Solving the Problems

As a result of thorough investigation, the present inventors conceived a novel configuration for a transfer-membrane retaining jig that retains a transfer membrane in a separation-transfer device that performs direct blotting.

In other words, a transfer-membrane retaining jig according to one aspect of the present invention is a transfer-membrane retaining jig for retaining a transfer membrane in a separation-transfer device that separates analyte by way of electrophoresis, dispenses the analyte thus separated from a dispensing part, and transfers the analyte thus separated to the transfer membrane by causing the transfer membrane to abut the dispensing part and move, the transfer-membrane retaining jig including a fixing part that fixes at least one end in a movement direction of the transfer membrane, in which the fixing part includes: an elastic body that abuts the transfer membrane from an opposite side to the dispensing part; and a pressing member that presses the transfer membrane against the elastic body.

Effects of the Invention

According to an embodiment of the present invention, it is possible to cause a transfer membrane to closely contact a dispensing part suitably.

PREFERRED MODE FOR CARRYING OUT THE INVENTION

An embodiment of the present invention is as follows when explaining based on the drawings.

Figure 1:
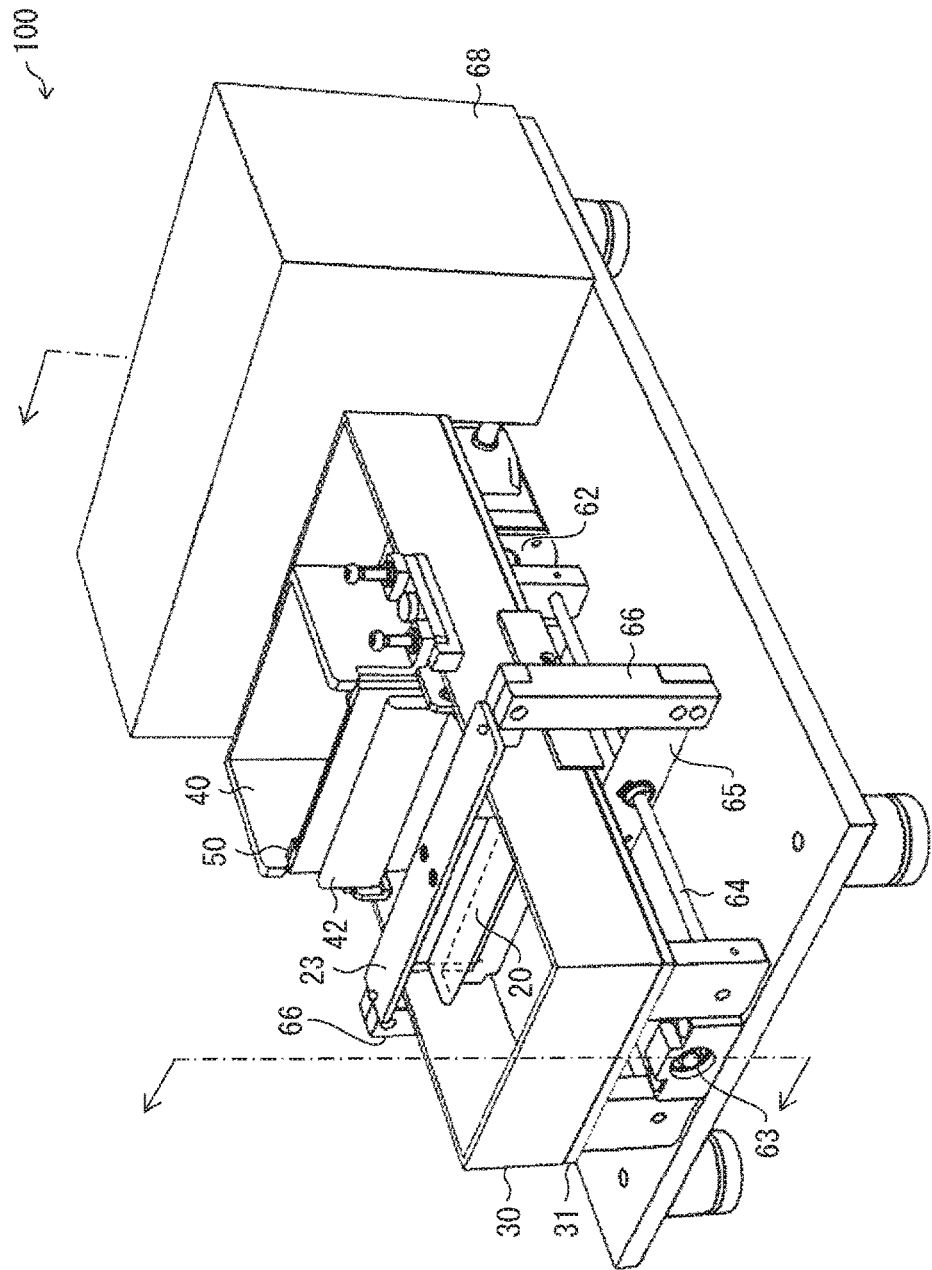
FIG. 1 is a perspective view showing an outline configuration of a separation-transfer device according to an embodiment of the present invention.
Figure 2:
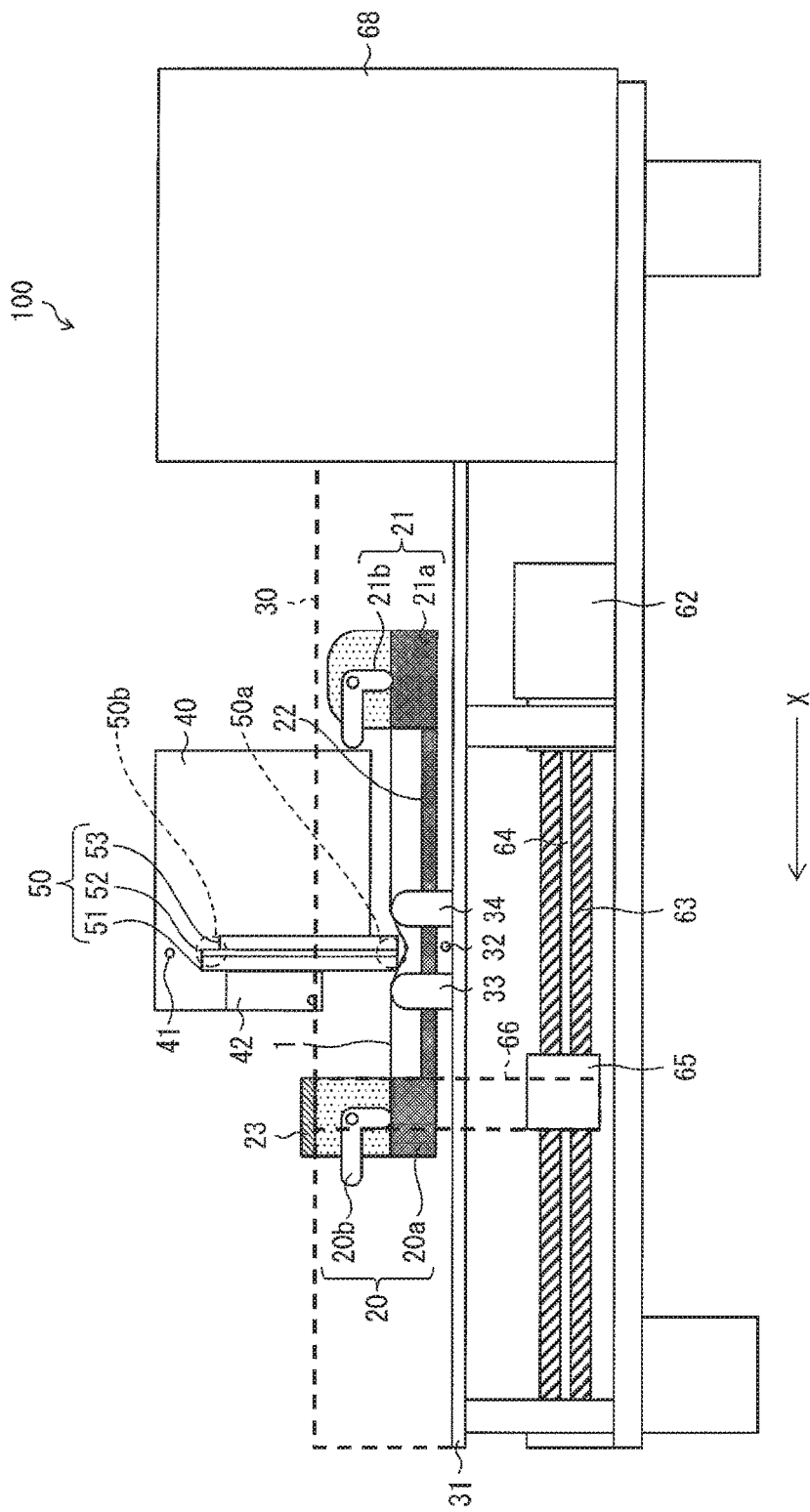
FIG. 2 is a cross-sectional view showing an outline configuration of a separation-transfer device according to an embodiment of the present invention.

First, a schematic configuration of a separation-transfer device 100 according to the present embodiment will be explained by referencing FIGS. 1 and 2. FIG. 1 is a perspective view schematically showing the configuration of the separation-transfer device 100. FIG. 2 is a cross-sectional view schematically showing the configuration of the separation-transfer device 100.

As shown in FIGS. 1 and 2, the separation-transfer device 100 is a separation-transfer device that separates an analyte by way of electrophoresis, dispenses the separated analyte from a dispensing part, and transfers the separated analyte to a transfer membrane by causing the transfer membrane to abut with the dispensing part and causing to move, and includes a clamp (fixing part, first fixed part, arm part) 20, clamp (fixing part, second fixing part, arm part) 21, clamp frame (arm part, connection part) 22, carrier (arm part, portion wrapping around upper ends of side walls, second portion) 23, anode buffer tank (first buffer solution tank) 30, table 31, cathode buffer tank (second buffer solution tank) 40, separation unit 50, motor (drive unit) 62, ball screw (drive unit) 63, guide shaft (drive unit) 64, shaft holder (drive unit) 65, guide pole (arm part, first portion) 66, and control unit 68. In addition, although not illustrated for explanation, a lid covering the entirety during operation is further included for safety.

Herein, the separation unit 50 accommodates separation gel (separation medium) 52, and has a first opening (dispensing part) 50a that opens within the anode buffer tank 30 and a second opening 50b that opens within a cathode buffer tank 40. In addition, a transfer membrane 1 is arranged inside of the anode buffer tank 30 so as to face the first opening 50a. Furthermore, an anode (first electrode) 32 is arranged within the anode buffer tank 30, and a cathode (second electrode) 41 is arranged within the cathode buffer tank 40.

For this reason, with the separation-transfer device 100, the cathode 41 within the cathode buffer tank 40 and the anode 32 within the anode buffer tank 30 are electrically connected via the buffer solutions of the two tanks, separation gel 52 and transfer membrane 1, by filling buffer solutions into the cathode buffer tank 40 and anode buffer tank 30. In other words, the separation-transfer device 100 is a device that separates a sample introduced from the second opening 50b by way of the separation gel 52 and causes each separated component to be dispensed from the first opening 50a and adsorb to the transfer membrane 1, by applying a voltage between the cathode 41 and anode 32.

Hereinafter, the respective principle members will be explained in detail by referencing FIGS. 1 and 2.

(Anode and Cathode)

The anode 32 is arranged within the anode buffer tank 30, and the cathode 41 is arranged within the cathode buffer tank 40. The anode 32 and cathode 41 are formed from a material having electrical conductivity such as a metal. As the material forming the anode 32 and cathode 41, for example, platinum is preferred from the viewpoint of suppressing ionization of the electrodes.

The electrode arrangements of these are not particularly limited so long as the anode 32 is arranged within the anode buffer tank 30 and the cathode 41 is arranged within the cathode buffer tank 40; however, for example, the cathode 41, first opening 50a and anode 32 may be arranged on substantially the same straight line. In such an arrangement, so long as the transfer membrane 1 is arranged as shown in FIG. 1, the precision of sample adsorption can be improved since the line of electric force passing through the first opening 50a will be substantially vertical relative to the transfer membrane 1.

In addition, the anode 32 is preferably arranged to be distanced from the transfer membrane 1. It is thereby possible to suppress the bubbles generating from the anode 32 from negatively influencing the adsorption of separated components on the transfer membrane 1.

The anode 32 and cathode 41, for example, may be used by connecting to the control unit 68, or may be used by connecting to an external power supply (DC power source). In the case of using by connecting to an external power supply, after setting the time, current and voltage in the power supply, the control unit 68 may be operated to cause the separation-transfer device 100 to start operation at the same time as operation initiation of the power supply.

(Anode Buffer Tank and Cathode Buffer Tank)

The anode buffer tank 30 and cathode buffer tank 40 are insulative containers storing the buffer solution (buffer). The cathode buffer tank 40 is provided above the anode buffer tank 30. It should be noted that, in the present embodiment, the anode buffer tank 30 is fixed on the table 31, and the cathode buffer tank 40 is fixed to the anode buffer tank 30; however, the present invention is not limited to this configuration.

The buffer solutions filled in the anode buffer tank 30 and cathode buffer tank 40 can be any buffer solution having electrical conductivity, and particularly, a buffer solution having a buffering region of weakly acidic to weakly basic can be suitably used. As such a buffer solution, for example, it is possible to use buffer solutions such as a Tris/glycine-based buffer solution, acetic acid buffer solution, sodium carbonate-based buffer solution, CPS buffer solution, Tris/boric acid/EDTA buffer solution, Tris/acetic acid/EDTA buffer solution, MOPS, phosphoric acid buffer solution, and Tris/tricine-based buffer solution.

In addition, although the details are described later, guides (support members) 33, 34 supporting the transfer membrane 1 from the back surface of the transfer membrane 1 (face on an opposite side to the separation unit 50) are provided to the bottom part of the anode buffer tank 30 in the movement path of the transfer membrane 1.

(Separation Unit)

The separation unit 50 accommodates the separation gel (separation medium) 52 inside thereof. In the present embodiment, the separation unit 50 is standing in a substantially vertical direction, and the lower part thereof is arranged within the anode buffer tank 30, and the upper part thereof is arranged so that one side contacts the cathode buffer tank 40. The separation gel 52 is thereby liquid-cooled by at least one of the buffer solution within the anode buffer tank 30 and the buffer solution within the cathode buffer tank 40, and can be sufficiently cooled.

In addition, the separation unit 50 has the first opening 50a that opens within the anode buffer tank 30, and the second opening 50b that opens within the cathode buffer tank 40. It is thereby configured so that the separation gel 52 faces inside the anode buffer tank 30 via the first opening 50a, and faces inside the cathode buffer tank 40 via the second opening 50b. It should be noted that, in the present embodiment, the separation unit 50 is fixed to the cathode buffer tank 40 by the lock 42 provided to the cathode buffer tank 40; however, the present invention is not limited to this configuration.

The separation unit 50 can be configured from two insulating plates 51, 53 formed from insulators such as glass or acrylic. In one embodiment, the separation unit 50 exposes the separation gel 52 by a part of the insulating plate 53 being notched out at the second opening 50b, whereby sample can be easily introduced to the separation gel 52.

The separation gel 52 is a gel for separating the sample components introduced from the second opening 50b according to the molecular weight. The separation gel 52 can be filled into the separation unit 50 prior to installation of the separation unit 50 to the separation-transfer device 100, or after installing. In addition, a commercially available PAGE chip into which the separation gel 52 is filled may be used as the separation unit 50. As an example of the separation gel 52, acrylamide gel, agarose gel and the like are exemplified. The width of the separation gel 52 can be established as a length enabling a 10- to 12-lane sample to be separated, for example.

It should be noted that, in the present embodiment, although a configuration filling the separation gel 52 into the separation unit 50 is being adopted, a configuration providing a large number of ultrafine posts called nano-pillars between the insulating plate 51 and insulating plate 53 can also be adopted.

It addition, the first opening 50a of the separation unit 50 may be covered by a coating part formed by an electrically conductive porous material (hydrophilic PVDF (polyvinylidene difluoride) film), hydrophilic PTFE (polytetrafluoroethylene) film, etc.), including the circumference thereof. In the case of the transfer membrane 1 contacting or being pushed against the first opening 50a (case of not providing a distance between the first opening 50a and transfer membrane 1), the transfer membrane 1 can reduce the frictional resistance and damage incurred from the separation unit 50 and separation gel 52 when the transfer membrane 1 is conveyed.

It should be noted that, by the separation unit 50 standing in a substantially vertical direction, the separation unit 50 can greatly increase the sample introduction amount compared to a configuration being installed in a substantially horizontal direction. This is because, with the horizontal-type electrophoresis apparatus, it is difficult to change the depth of the well provided in the separation gel; however, with the vertical-type electrophoresis apparatus, since the depth of the well can be changed easily, the sample introduction amount can be made to increase easily.

(Transfer Membrane 1)

It is preferable for the transfer membrane 1 to be an absorbing/retaining body of samples that enables to stably preserve a sample separated by the separation gel 52 over a long period, and further, facilitates subsequent analysis. As the material of the transfer membrane 1, it is preferably a material having high strength, and having high sample binding capacity (adsorbable weight per unit volume). As the transfer membrane 1, a PVDF membrane or the like is suited in the case of the sample being protein. It should be noted that it is preferable to perform hydrophilization treatment using methanol or the like in advance on the PVDF membrane. Otherwise, a membrane conventionally used in the adsorption of proteins, DNA and nucleic acids such as a nitrocellulose membrane or nylon membrane can also be used.

It should be noted that, the samples that can be separated and adsorbed in the separation-transfer device 100 are not particularly limited to these; however, a preparation from biological material (e.g., biont, body fluid, cell strain, tissue culture, or tissue fragment), a commercially available reagent, and the like can be exemplified. For example, polypeptides or polynucleotides can be exemplified.

The transfer membrane 1 is used in a state immersed in the buffer solution within the anode buffer tank 30.

In the present embodiment, the transfer membrane 1 is adequate so long as having a length used in one-time electrophoresis/transfer, i.e. length of a distance moved within the anode buffer tank 30 in the one-time electrophoresis/transfer. By configuring the transfer membrane 1 in this way, an operation to cut the transfer membrane 1 for every one-time electrophoresis/transfer becomes unnecessary, and thus the usability of the separation-transfer device 100 can be improved. In addition, the width of the transfer membrane 1 is sufficient so long as established as a length corresponding to the width of the separation gel 52.

(Adjuster)

In the present embodiment, the transfer membrane 1 is used in a state retained by the adjuster (transfer-membrane retaining jig) 2. The adjuster 2 includes the clamps 20, 21 and the clamp frame 22, and is arranged at an inner side of the side walls of the anode buffer tank 30.

FIG. 3 is a cross-sectional view showing an outline configuration of the adjuster 2, with (A) showing a state in which the clamps 20, 21 are not fixing the transfer membrane 1, and (B) showing a state in which the clamps 20, 21 are fixing the transfer membrane 1. As shown in FIG. 3, the clamps 20, 21 come to fix the ends 1a, 1b in the movement direction of the transfer membrane 1, respectively.

Figure 3A:
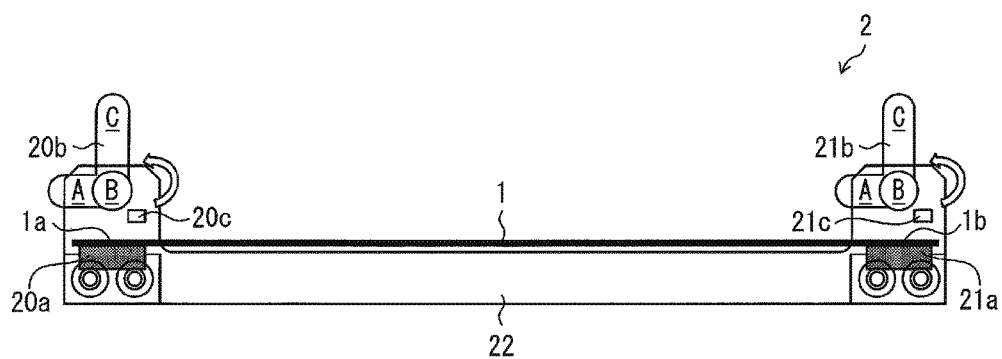
FIG. 3 is a cross-sectional view showing an outline configuration of a transfer-membrane retaining jig according to an embodiment of the present invention.
Figure 3B:
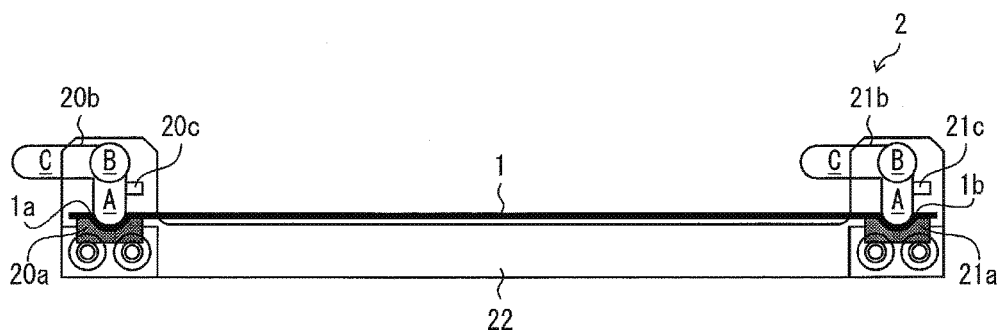

As shown in FIG. 3(B), the clamp 20 includes an elastic body 20a, a pressing member 20b and stopper (latching member) 20c, and fixes the transfer membrane 1 by causing the elastic body 20a to abut with the back face of the transfer membrane 1 (face on opposite side to face abutting the first opening 50a), and pressing the transfer membrane 1 (end 1a thereof) from a surface side of the transfer membrane 1 against the elastic body 20a by way of the pressing member 20b. In particular, it is preferable for the pressing member 20b to be made to push the transfer membrane 1 into the elastic body 20a.

In more detail, as shown in FIGS. 3(A) and (B), the pressing member 20b comes to rotate counter-clockwise, in the page view, about the shaft B, which is orthogonal to the movement direction, and spaced from the transfer membrane 1 at an opposite side to the elastic body 20b, and includes an abutting part A that abuts the transfer membrane 1 and presses the transfer membrane 1 to the elastic body 20a accompanying this rotation.

The rotation of the pressing member 20b for fixing the transfer membrane 1 is made from a state in which the abutting part A is spaced from the elastic body 20a (FIG. 3(A)) until a state sinking into the elastic body 20a (FIG. 3(B)). The stopper 20c is a latching member defining the range of rotation of the pressing member 20b, and comes to lock so that the pressing member 20b does not rotation upon entering a state in which the abutting part A sinks into the elastic body 20a, and fixes the transfer membrane 1.

Similarly, as shown in FIG. 3(B), the clamp 21 includes the elastic body 21a, pressing member 21b and stopper (latching member) 21c, and fixes the transfer membrane 1 by bringing the elastic body 21a into contact with the back face of the transfer membrane 1 (face on opposite side to face abutting the first opening 50a), and pressing the transfer membrane 1 (end 1a thereof) from the surface side of the transfer membrane 1 to the elastic body 20a by way of the pressing member 21b. In particular, it is preferable for the pressing member 21b to push the transfer membrane 1 against the elastic body 21a.

In more detail, as shown in FIGS. 3(A) and (B), the pressing member 21b comes to rotate counter-clockwise, in the page view, about the shaft B, which is orthogonal to the movement direction, and spaced from the transfer membrane 1 at an opposite side to the elastic body 21b, and includes an abutting part A that abuts the transfer membrane 1 and presses the transfer membrane 1 to the elastic body 21a accompanying this rotation.

The rotation of the pressing member 21b for fixing the transfer membrane 1 is made from a state in which the abutting part A is distanced from the elastic body 21a (FIG. 3(A)) until a state sinking into the elastic body 21a (FIG. 3(B)). The stopper 21c is a latching member defining the range of rotation of the pressing member 21b, and comes to latch so that the pressing member 21b does not rotate upon entering a state in which the abutting part A sinks into the elastic body 21a, and fixes the transfer membrane 1.

In addition, the pressing members 20a, 20b further include a handle part C for a user to perform the above-mentioned rotation operation. The shape of the handle part C is not particularly limited; however, it is acceptable so long as a configuration extending from the shaft B in a different direction than the direction in which the abutting part A extends, and is preferably made a configuration extending in a direction orthogonal to the direction in which the abutting part A extends so as to make an L-shape with the pressing members 20a, 20b as main bodies, and the shaft B as the corner part. It is thereby possible to make the handle part of the pressing members 20b, 21b horizontal, and the height of the pressing members 20b, 21b short, in the state rotating the pressing members 20a, 20b about the shaft B to fix the transfer membrane 1. Upon direct blotting, the pressing members 20b, 21b move in the anode buffer tank 30 in a state fixing the transfer membrane 1; however, by making the heights of the pressing members 20b, 21b at this time short, it is possible to suppress waves from rippling in the anode buffer due to the moving pressing members 20b, 21b. It is thereby possible to more favorably perform transfer.

Figure 4:
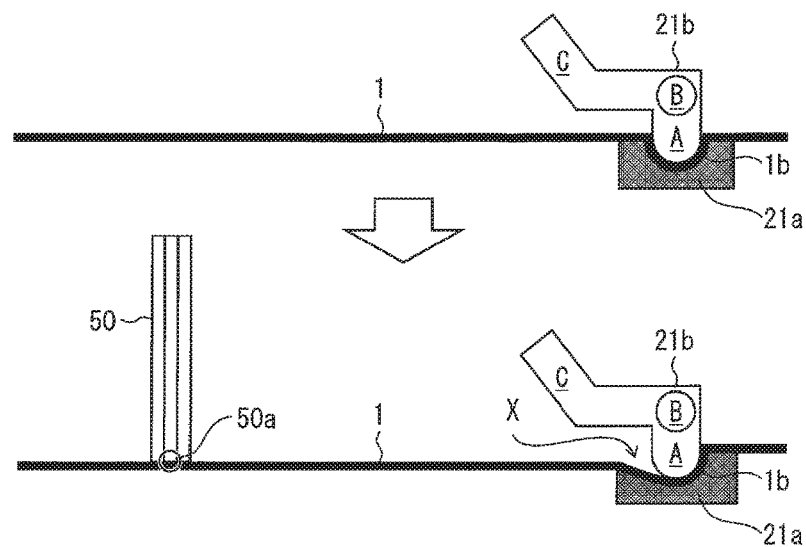
FIG. 4 is a cross-sectional view illustrating functions of the transfer-membrane retaining jig of the embodiment of the present invention.
Figure 5:
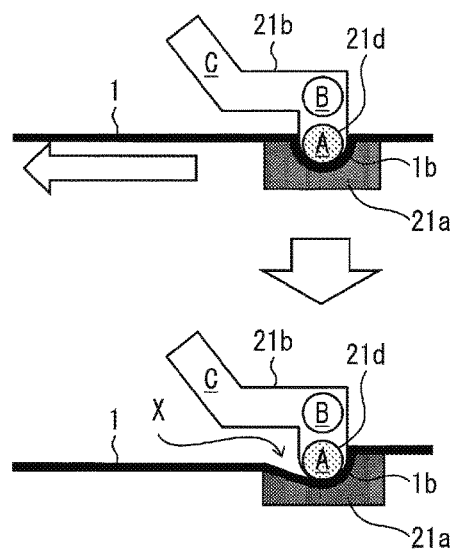
FIG. 5 is a cross-sectional view illustrating functions of the transfer-membrane retaining jig of the embodiment of the present invention.

It should be noted that the handle part C is not necessarily a linear shape, and may be curved so as to facilitate holding by the hand of a user, as shown in FIGS. 4 and 5.

Herein, the function of the adjuster 2 will be explained. The adjuster 2 is a structure that retains the transfer membrane 1, and is preferably configured so as to maintain a state in which the tension on the transfer membrane 1 is as high as possible. This is because, if the tension on the transfer membrane 1 is low (transfer membrane is loose), even if causing the transfer membrane 1 to abut with the first opening 50a of the separation unit 50, it will be difficult to bring the transfer membrane 1 into close contact with the first opening 50a. As explained below, the adjuster 2 according to the present embodiment comes to suitably maintain the tension of the transfer membrane 1, and can easily bring the transfer membrane 1 into close contact with the first opening 50a.

FIG. 4 is a cross-sectional view illustrating functions of the adjuster 2. In the state retaining the transfer membrane 1 by way of the adjuster 2, i.e. state fixing the transfer membrane 1 by way of the clamps 20, 21, when the transfer membrane 1 abuts the first opening 50a of the separation unit 50, the transfer membrane 1 is depressed by the first opening 50a, and at an inner side of the fixing position of the clamps 20, 21 (X in the drawing), the elastic bodies 20a, 20a are depressed by the transfer membrane 1, which was depressed. At this time, since a resilient force from the elastic bodies 20a, 21a is acting on the transfer membrane 1, it is possible to maintain the tension on the transfer membrane 1. It is thereby possible to suitably bring the transfer membrane 1 into close contact with the first opening 50a.

In addition, as shown in FIGS. 3(A) and (B), the pressing member 20b of the clamp 20 comes to press the transfer membrane 1 against the elastic body 20a by rotating so as to drag the transfer membrane 1 in a direction from the end 1a of the transfer membrane 1 towards the end 1b. In other words, the transfer membrane 1 is dragged in a direction towards the inner side (loosening direction) during fixing of the clamp 20. On the other hand, the pressing member 20b of the clamp 21 comes to press the transfer membrane 1 against the elastic body 21a by rotating so as to drag the transfer membrane 1 from the end 1a of the transfer membrane 1 towards the end 1b. In other words, the transfer membrane 1 is dragged in a direction towards the outer side (tightening direction) during fixing of the clamp 21.

At this time, by configuring so as to first fix the transfer membrane 1 by the clamp 20, and subsequently fix the clamp 21, it is possible to successfully apply suitable tension to the transfer membrane 1. This is because, during fixing by the clamp 20, since the transfer membrane 1 is not being fixed by the clamp 21, even if dragged to the inner side by the clamp 20, the transfer membrane 1 simply moves. Then, subsequently, in a state tightening the transfer membrane 1 as much as possible, the transfer membrane 1 is further dragged to the outer side by performing fixing by the clamp 21, whereby it is possible to further raise the tension on the transfer membrane 1. In this way, by at least one of the clamps (clamp 21 in the present embodiment) coming to drag the transfer membrane 1 to the outer side during fixing, it is possible to raise the tension on the transfer membrane 1. It is thereby possible to suitably bring the transfer membrane 1 into close contact with the first opening 50a.

In addition, the pressing member 20b of the clamp 20 comes to rotate so as to drag the transfer membrane 1 to the inner side during fixing of the transfer membrane 1, and by the stopper 20c being further provided, after rotation is locked by the stopper 20c, the transfer membrane 1 is prevented from shifting to the inner side (loosening). It is thereby possible to suitably prevent the transfer membrane 1 from loosening when a strong force acts on the fixed transfer membrane 1.

In addition, in a modified example, in order to prevent the transfer membrane 1 from shifting while fixing, an anti-slip member may be provided to the abutting part A of the pressing members 20b, 21b. As the anti-slip member, it is possible to use a well-known member having a high friction coefficient and, for example, an anti-slip seal may be adhered to the abutting part.

In addition, as shown in FIG. 5, anti-slip members 20d, 21d such as a silicone sponge may be embedded in the abutting part A of the pressing members 20b, 21b. It is thereby possible for the anti-slip members 20d, 21d to prevent peeling from the pressing members 20b, 21b.

Figure 6:
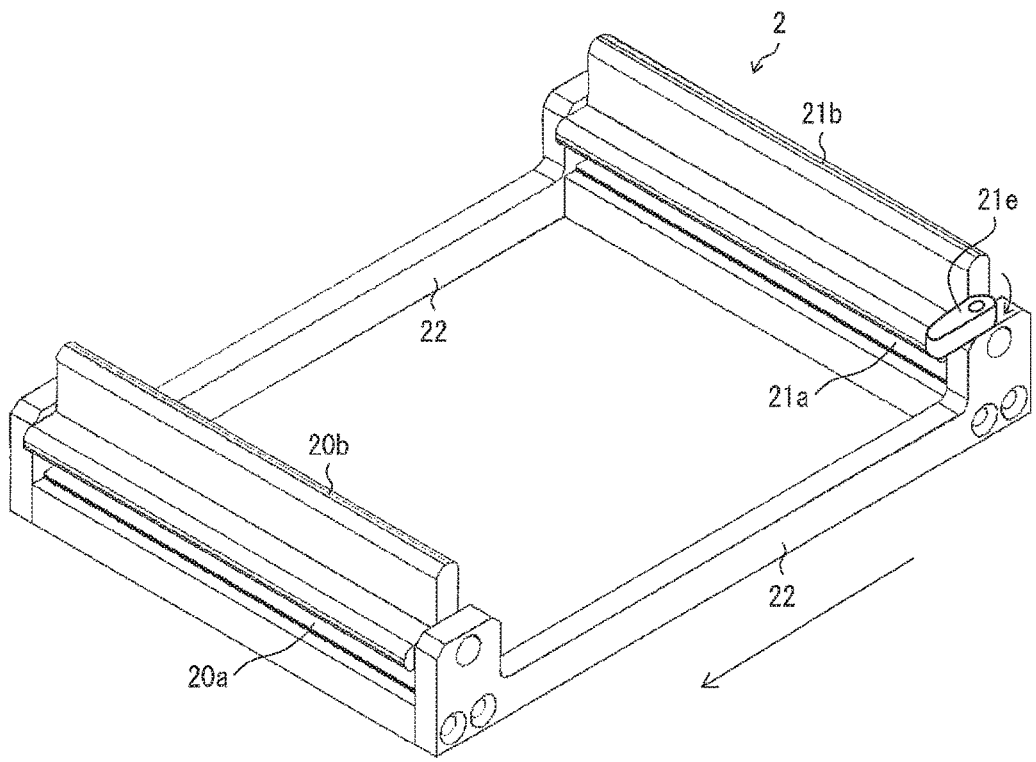
FIG. 6 is a perspective view showing an outline configuration of a transfer-membrane retaining jig according to an embodiment of the present invention.

In addition, in the modified example, the clamp 21 may include a lock (latching member) 21e, as shown in FIG. 6. The lock 21e is a latching member for preventing the pressing member 21b from returning after causing the pressing member 21b to rotate and fixing the transfer membrane 1, and can suitably prevent the transfer membrane 1 from loosening when a strong force acts on the fixed transfer membrane 1, by providing the lock 21e.

So long as being elastic bodies having a softness that enables the sinking in of the pressing members 20b, 21b and transfer membrane 1, and that can fix the transfer membrane 1 by forming pairs with the pressing members 20b, 21b, the material of the elastic bodies 20a, 21a is not particularly limited; however, for example, it is possible to suitably use an elastomer such as silicone sponge, urethane rubber, chloroprene rubber and fluorine rubber.

In one example, the properties of the silicone sponge used in the elastic bodies 20a, 21a can be an apparent density (JIS-K6767) of 0.50 g/cm$^3$, tensile strength (JIS-K6251) of 1.6 MPa, and hardness (Type E, JIS-K6253) of 30. The properties of the elastic bodies 20a, 21a are not limited thereto; however, they can be an apparent density (JIS-K6767) of 0.1 to 1.0 g/cm$^3$, tensile strength (JIS-K6251) of 0.3 to 3.0 MPa, and hardness (Type E, JIS-K6253) of 10 to 100.

Figure 7A:
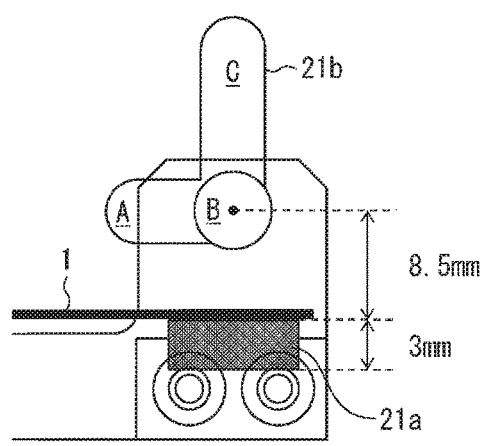
FIG. 7 is a cross-sectional view illustrating an example of the dimensions of the transfer-membrane retaining jig according to an embodiment of the present invention.
Figure 7B:
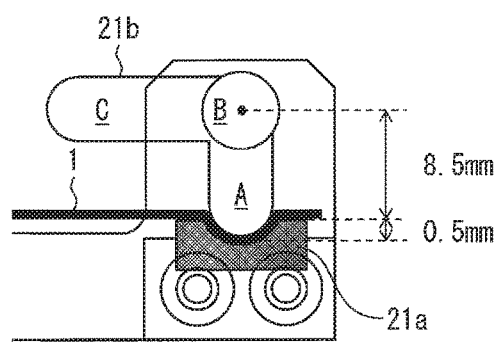

In addition, the dimensions of each constituent element of the adjuster 2 are not particularly limited; however, the shaft B for rotation of the pressing member 20b (or 21b) is preferably close to the elastic body 20a (or 21a). If the distance between the shaft B for rotation of the pressing member 20b (or 21b) and the elastic body 20a (or 21a) is long, based on the principle of leverage, the transfer membrane 1 may tend to deviate from the clamp 20 (or 21). FIG. 7 is a view showing an example for the dimensions of the adjuster 2. Although the distance from the shaft B of the pressing member 21b to the elastic body 21a is set to 8.5 mm in one example as shown in FIG. 7, it is not limited thereto. In addition, although the thickness of the elastic body 21a can be set to 3 mm, and the indenting distance of the elastic body 21a by the pressing member 21b set to 0.5 mm in one example, they are not limited thereto.

By interposing the transfer membrane 1 between the pressing member 20b, 21b which is harder than the elastic body 20a, 21a, and the elastic body 20a, 21a, it is possible to impart tension on the transfer membrane 1 by the transfer membrane 1 sinking into the elastic bodies 20a, 21a, when causing the transfer membrane 1 to abut the first opening 50a of the separation unit 50. It is thereby possible to suitably bring the transfer membrane 1 into close contact with the first opening 50a.

In addition, since the transfer membrane 1 is wound in and fixed by causing the pressing member 21b to rotate so as to wind in the transfer membrane 1 to the outer side upon fixing the end 1b after fixing the end 1a of the transfer membrane 1, it is possible to fix the transfer membrane 1 without slack.

According to the adjuster 2 according to the present embodiment, since it is possible to fix the transfer membrane 1 without slack, and further, for tension to act on the transfer membrane 1 when causing the transfer membrane 1 to abut the first opening 50a in this way, the close contact between the first opening 50a and transfer membrane 1 as a result thereof becomes uniform, and thus molecules of the analysis target (analyte) can be favorably transferred to the transfer membrane 1.

The clamp frame 22 is a shaft member connecting the clamps 20, 21, and connects the clamps 20, 21 to be separated by a predetermined distance. It is thereby possible to tighten the transfer membrane 1 without slack along the movement direction thereof, when fixing both ends of the transfer membrane 1 by the clamps 20, 21. It is thereby possible to suppress the transfer results from blurring due to slack in the transfer membrane 1, and thus improve the measurement sensitivity. In addition, it is possible to make the tension acting on the transfer membrane 1 conveyed accompanying movement of the clamp 20 to be constant. Therefore, it is possible to more suitably transfer a sample to the transfer membrane 1 without blurring.

The clamp frame 22 is arranged at a position sandwiching the transfer membrane 1 from the lateral side to the movement direction, whereby it is possible to avoid the clamp frame 22 from overlapping the top surface (face opposing the first opening 50a) and back surface (facing on opposite side to first opening 50a) of the transfer membrane 1. It is thereby possible to prevent transfer from the separation gel 52 to the transfer membrane 1, abutting of other members with the back surface of the transfer membrane 1, etc. (details described later) being inhibited by the clamp frame 22. In addition, the fixing of the transfer membrane 1 by the clamps 20, 21 will not be inhibited either.

The clamp frame 22 and clamps 20, 21 (excluding elastic bodies 20a, 21a) are not limited thereto; however, for example, it is possible to constitute from synthetic resins such as Teflon (registered trademark), acrylic resin and PEEK resin.

(Arm Part)

In the present embodiment, the adjuster 2 is built into the arm part. The arm part causes the transfer membrane 1 to move and abut the first opening 50a. In the present embodiment, the arm part is configured from the adjuster 2, carrier 23 and guide poles 66, which are a series of connected members.

The guide pole 66 is a shaft member that is arranged so as to connect to a drive unit described later (shaft holder 65), and pass to outside of a side wall of the anode buffer tank 30. The carrier 23 is a member that connects to the guide pole 66, and connects to the clamp 20 by going around the upper end of the side wall of the anode buffer tank 30.

In the above way, the arm part passes along the outer sides of the side walls of the anode buffer tank 30 from a position connecting to the drive unit, wraps around the upper ends of the side walls, and links at the inner sides of the side walls.

It should be noted that, although not to limit the present invention, in the present embodiment, the guide poles 66 extend at outer sides of the side walls of the anode buffer tank 30 until positions aligning with the upper ends of the side walls. Then, the carrier 23 fits together with the guide poles 66, and extends to an inner side of the side wall by spanning over the upper ends of the side walls of the anode buffer tank 30.

By configuring in this way, the carrier 23 can attach and detach easily to the drive unit. The guide poles 66 are arranged at the outer side of the side walls of the anode buffer tank 30, and do not become obstructions to various operations such as detachment of the anode buffer tank 30 (details explained in second embodiment), or setting of electrodes, which are performed as necessary. For this reason, it is possible to successfully perform various operations by removing the carrier 23 as appropriate.

(Drive Unit)

The drive unit drives the arm part in a substantially horizontal direction, and is configured by a motor 62, ball screw 63, guide shaft 64 and shaft holder 65 in the present embodiment.

The motor 62 causes the ball screw 63 to rotate. The motor 62 may employ one that can vary rotation speed, and may employ one of fixed rotation speed in combination with gears. The ball screw 63 threads with the shaft holder 65 along with penetrating the shaft holder 65. The guide shaft 64 penetrates the shaft holder 65, and the shaft holder 65 is configured to be movable along the guide shaft 64. Then, by the motor 62 causing the ball screw 63 to rotate, the shaft holder 65 is driven in the X direction in the drawing (substantially horizontal direction). The shaft holder 65 connects with the arm part (guide pole 66), whereby the drive unit can drive the arm part in the X direction in the drawing (substantially horizontal direction). Then, due to the arm part retaining the transfer membrane 1, the transfer membrane 1 moves in the X direction in the drawing (substantially horizontal direction).

However, the present invention is not limited thereto, and so long as being able to drive the arm part in a substantially horizontal direction, the drive unit may be configured by another drive mechanism (e.g., belt, gears, etc.).

In addition, the drive unit is provided below the anode buffer tank 30. It is thereby possible to prevent the risk of the buffer solution having scattered from the anode buffer tank 86 from causing the durability of the drive unit to decline, and the risk of the drive unit becoming a hindrance to various operations on the separation-transfer device 100.

(Control Unit)

The control unit 68 is a control panel that performs various controls of the separation-transfer device 100 (control of the position of the arm part, control of current/voltage applied to the anode 32 and cathode 41, etc.). The control unit 68 may include buttons and switches for receiving inputs from a user, and lamps, a display unit, etc. for notifying the operating state to the user.

(Electrophoresis and Transfer of Sample)

Next, the flow of electrophoresis and transfer of sample in the separation-transfer device 100 will be explained by referencing FIG. 1. As shown in FIG. 1, during the electrophoresis and transfer of sample, the transfer membrane 1 is retained in a state arranged at a position opposing the first opening 50a by the adjuster 2. At this time, the transfer membrane 1 is supported from the back surface of the transfer membrane 1 (opposite side to the separation unit 50), by the guides 33, 34 provided at the bottom part of the anode buffer tank 30.

The guides 33 and 34 are provided at the bottom part of the anode buffer tank 30 so as to support the transfer membrane in the movement path on which the transfer membrane 1 moves. The guides 33 and 34 have a longitudinal direction that is orthogonal to the movement direction (X direction) of the transfer membrane 1, and are parallel to the longitudinal direction of the first opening 50a.

Then, by the separation unit 50 (side of the first opening 50a thereof) abutting the top surface of the transfer membrane 1 (side of the separation unit 50 thereof), the transfer membrane 1 is bent so that an opposite side to the separation unit 50 becomes convex. In this way, the transfer membrane 1 is supported by the guides 33 and 34, the separation unit 50 pushes this down to be bent so as to become convex downwards (opposite side to the separation unit 50). It is thereby possible for the tension to act on the transfer membrane 1, to cause the transfer membrane 1 to be in more close contact with the first opening 50a. It is thereby possible to more appropriately perform transfer from the separation gel 52 to the transfer membrane 1.

In particular, by the guides 33 and 34 being respectively formed at positions interposing a position opposing the first opening 50a on the bottom part of the anode buffer tank 30 to form a pair, the transfer membrane 1 is supported by the guides 33 and 34 arranged at both sides of the separation unit 50, the separation unit 50 pushes this down to be bent so as to become convex downward (opposite side to the separation unit). It is thereby possible for tension to more uniformly act on the transfer membrane 1 to cause the transfer membrane 1 to be more uniformly in close contact with the opening 50a. It is thereby possible to more appropriately perform transfer from the separation gel 52 to the transfer membrane 1.

It should be noted that, as mentioned above, the clamp frame 22 is arranged at positions interposing the transfer membrane 1 from lateral sides to the movement direction, and thus will not hinder the guides 33 and 34 from supporting the transfer membrane 1 from the back surface thereof.

Then, the sample is introduced to the separation gel 52 from the second opening 50b of the separation unit 50. In addition to biomolecules serving as the analysis target, it is preferable to add a visible molecular weight marker for confirming the progress of electrophoresis to the sample.

In the above state, separation is performed by electrophoresis of the sample. The control unit 68 controls the motor 62 to set the position of the transfer membrane 1 at the start position, and then flow electric current between the anode 32 and cathode 41 to start electrophoresis. The electric current value flowing between the anode 32 and cathode 41 is not particularly limited; however, it is preferably no more than 50 mA, and more preferably at least 20 mA to no more than 30 mA. It should be noted that it may control so that the electric current value becomes constant, may be controlled so that the voltage becomes constant, or the current and voltage may be controlled in other modes.

The transfer membrane 1 is moved gradually towards the X direction (substantially horizontal direction) by driving of the arm part (adjuster) by the drive unit, according to the progress of electrophoresis in the separation unit 50. The X direction is a direction orthogonal to the longitudinal direction of the first opening 50a. Although the movement speed of the transfer membrane 1 is not particularly limited, it is possible to set a pace of moving 5 to 10 cm in 60 to 120 minutes, for example.

Then, the sample dispensed according to electrophoresis from the first opening 50a (sample separated in separation gel 52) is adsorbed at positions (positions opposing the first opening 50a at the dispensed timing) according to the timing of dispensing to the transfer membrane 1. The separated sample is thereby transferred to the transfer membrane 1.

After transfer, it is possible to recover the transfer membrane 1, and supply to staining, immunoreaction (blotting and antigen-antibody reaction by Western blotting) or the like. Subsequently, the separation pattern of components transferred to the transfer membrane 1 is detected by a fluorescence detector. Such a fluorescence detector may be included in the separation-transfer device 100, whereby it is possible to automate the entire process of electrophoresis, transfer and detection.

By establishing a configuration in which the separation unit 50 is standing up substantially vertically in above way, it is possible for the separation unit 50 to be immersed in the buffer solution of at least one among the anode buffer tank 30 and cathode buffer tank 40, and thus liquid-cool the separation gel 52.

Then, in the case of configuring the separation-transfer device 100 in this way, (i) it is necessary to cause the transfer membrane 1 to move within the anode buffer tank 30, (ii) in the case of trying to arrange the drive unit upstream of the transfer membrane 1 as in the conventional technology, there is a risk of the buffer solution having scattered from the anode buffer tank 30 causing the durability of the drive unit to decline, and a risk of the drive unit becoming a hindrance to various operations on the separation-transfer device 100; however, (iii), with the present embodiment, by providing the drive unit under the anode buffer tank 30, and making the form of the arm part into a form that passes along the outer sides of the side walls of the anode buffer tank 30, wraps around the upper ends of the side walls and then links at the inner sides of the side walls, it is possible to cause the transfer membrane 1 to move successfully within the anode buffer tank 30, while avoiding a decline in the durability of the drive unit due to the buffer solution and the hindrance of various operations by the drive unit.

(Summary)

The transfer-membrane retaining jig (adjuster 2) according to a first aspect of the present invention is a transfer-membrane retaining jig for retaining a transfer membrane 1 in a separation-transfer device 100 that separates analyte by way of electrophoresis, dispenses the analyte thus separated from a dispensing part (first opening 50a), and transfers the analyte thus separated to the transfer membrane by causing the transfer membrane to abut the dispensing part and move, the transfer-membrane retaining jig including a fixing part (clamp 20, 21) that fixes at least one end in a movement direction of the transfer membrane, in which the fixing part includes: an elastic body 20a, 29b that abuts the transfer membrane from an opposite side to the dispensing part; and a pressing member 20b, 21b that presses the transfer membrane against the elastic body.

According to the above-mentioned configuration, the elastic body abuts against the end of the transfer membrane from the opposite side to the dispensing part, and this end is fixed by the pressing member pressing this end against the elastic body. When the transfer membrane is made to abut the dispensing part, it is thereby possible for tension to act on the transfer membrane by the transfer membrane sinking into the elastic body. It is thereby possible to suitably cause the transfer membrane to closely contact the dispensing part.

According to a second aspect of the present invention, in the transfer-membrane retaining jig of the first aspect, the pressing member 20b, 21b may undergo rotation about a shaft B that is orthogonal to the movement direction and spaced from the transfer membrane 1 to an opposite side to the elastic body 20a, 21a, and may include an abutting part A that presses the transfer membrane 1 against the elastic body by abutting the transfer membrane, accompanying the rotation.

According to the above-mentioned configuration, it is possible to fix the transfer membrane by causing the pressing member to rotate.

According to a third aspect of the present invention, in the transfer-membrane retaining jig of the second aspect, the pressing member 20b, 21b may further include a handle part operated for the rotation.

According to the above-mentioned configuration, it is possible to cause the pressing member to rotate easily.

According to a fourth aspect of the present invention, in the transfer-membrane retaining jig of the third aspect, the pressing member 20b, 21b may have an L-shaped form with the shaft as a corner part.

According to the above-mentioned configuration, it is possible to cause the pressing member to rotate easily. In addition, since it is possible to reduce the height of the pressing member in a state fixing the transfer membrane 1, it is possible to suppress waves from rippling in the anode buffer due to the pressing member moving during direct blotting, and thus favorable transfer can be performed.

According to a fifth aspect of the present invention, the transfer-membrane retaining jig of the second to fourth aspects may further include a first fixing part (clamp 21) that fixes one end 1b in the movement direction of the transfer membrane, in which a pressing member 21b of the first fixing part comes to press the transfer membrane 1 against the elastic body 21a by rotating so as to drag the transfer membrane 1 in a direction from one other end 1a in the movement direction of the transfer membrane 1 towards the one end 1b.

According to the above-mentioned configuration, upon fixing one end of the transfer membrane by the first fixing part, the pressing member is rotated so as to drag (wind in) the transfer membrane towards the outer side (direction from other end towards the one end). For this reason, since the transfer membrane is dragged (rolled up) to the outer side and fixed by fixing the one end by way of the first fixing part, after fixing the other end of the transfer membrane, it is possible to fix the transfer membrane without slack.

According to a sixth aspect of the present invention, in the transfer-membrane retaining jig of the fifth aspect, the first fixing part may include a latching member (stopper 21c, lock 21e) that defines a range of rotation of the pressing member 21b of the first fixing part.

According to the above-mentioned configuration, it is possible to prevent the fixing by the pressing member of the first fixing part from unfastening, by defining the range of rotation of the pressing member of the first fixing part.

According to a seventh aspect of the present invention, the transfer-membrane retaining jig of the fifth or sixth aspect may further include a second fixing part (clamp 20) that fixes the other end, in which a pressing member 20b of the second fixing part comes to press the transfer membrane 1 against the elastic body 20a by rotating so as to drag the transfer membrane 1 in a direction from the other end 1b towards the one end 1a.

According to the above-mentioned configuration, even in a case of the pressing member being rotated so as to drag the transfer membrane towards the inner side (direction from other end towards the one end), upon fixing the other end of the transfer membrane by way of the second fixing part, since the pressing member is rotated so as to drag the transfer membrane to the outer side upon fixing one end of the transfer membrane by the first fixing part, after fixing the other end of the transfer membrane by way of the second fixing part, the one end is fixed by way of the first fixing part, whereby the transfer membrane is dragged to the outer side and fixed; therefore, it is possible to fix the transfer membrane without slack.

According to an eighth aspect of the present invention, in the transfer-membrane retaining jig of the seventh aspect, the second fixing part may include a latching member (stopper 20c) that defines a range of rotation of the pressing member 20b of the second fixing part.

According to the above-mentioned configuration, it is possible to prevent fixing by the pressing member of the second fixing part from unfastening by defining the range of rotation of the pressing member of the first fixing part.

According to a ninth aspect of the present invention, in the transfer-membrane retaining jig of the second to eighth aspects, an anti-slip member 20d, 21b may be provided to the abutting part A.

According to the above-mentioned configuration, it is possible to prevent the transfer membrane from shifting upon fixing of the transfer membrane.

According to a tenth aspect of the present invention, in the transfer-membrane retaining jig of the ninth aspect, the anti-slip member may be embedded in the abutting part A.

According to the above-mentioned configuration, it is possible to prevent the anti-slip member from separating from the abutting part.

A separation-transfer device according to an eleventh aspect of the present invention is a separation-transfer device that separates analyte by way of electrophoresis, dispenses the analyte thus separated from a dispensing part, and transfers the analyte thus separate to a transfer membrane by causing the transfer membrane to abut the dispensing part and move, the separation-transfer device including: the transfer-membrane retaining jig of the first to tenth aspects.

Similar effects as the above-mentioned first to tenth aspects are exerted by the above-mentioned configuration.

According to a twelfth aspect of the present invention, the separation-transfer device of the eleventh aspect may include: a first buffer solution tank; a second buffer solution tank arranged above the first buffer solution tank; a separation unit that stands up in a substantially vertical direction, in which a separation medium is accommodated, and having a first opening that opens within the first buffer solution tank and a second opening that opens within the second buffer solution tank; an arm part that retains the transfer membrane arranged at a position opposing the first opening; and a drive unit that is provided below the first buffer solution tank and drives the arm part in a substantially horizontal direction, in which the arm part passes along the outer sides of the side walls of the first buffer solution tank, wraps around the top ends of the side walls and then links at the inner sides of the side walls.

According to the above-mentioned configuration, by establishing a configuration in which the separation unit stands up substantially vertically, it is possible for the separation unit to be immersed in buffer solution in the first or second buffer solution tank to liquid-cool the separation medium. However, in the case of configuring the separation-transfer device in this way, it is necessary to make the transfer membrane move within the first buffer solution tank.

Herein, according to the above-mentioned configuration, by providing the drive unit under the first buffer solution tank, and making the form of the arm part into a form that passes along the outer sides of the side walls of the first buffer solution tank, wraps around the top ends of the side walls and then links at the inner sides of the side walls, it is possible to cause the transfer membrane to move successfully within the first buffer solution tank, while avoiding a decline in the durability of the drive unit due to the buffer solution and the hindrance of various operations by the drive unit.

According to a thirteenth aspect of the present invention, in the separation-transfer device of the twelfth aspect, the arm part may be linked to the drive unit, and may have a first portion extending at outer sides of the side walls until a position aligning with upper ends of the side walls, and a second portion that fits with the first portion, and extends to an inner side of the side walls by spanning the upper ends of the side walls.

According to the above-mentioned configuration, the second portion can be easily detached and attached relative to the drive unit. The first portion is arranged at the outer sides of the side walls of the first buffer solution tank, and thus will not become a hindrance to removal of the first buffer solution tank and various operations such as setting of the electrode. For this reason, it is possible to successfully perform various operations by unfastening the second portion as appropriate.

According to a fourteenth aspect of the present invention, in the separation-transfer device of the twelfth or thirteenth aspect, a first electrode may be disposed in the first buffer solution tank, a second electrode may be disposed in the second buffer solution tank, and the transfer membrane may be disposed so as to be interposed between the first opening and the first electrode.

According to the above-mentioned configuration, since it is possible to apply voltage between the first opening that opens within the first buffer solution tank and the second opening that opens within the second buffer solution tank, electrophoresis of analyte can be successfully performed. In addition, since the transfer membrane is interposed between the first opening and the first electrode, it is possible to successfully perform transfer of the separated analyte from the first opening to the transfer membrane.

The present invention is not to be limited the aforementioned embodiment, with various modifications being possible within the scope indicated by the claims, and embodiments obtained by appropriately combining the technical means disclosed in each of the different embodiments are also included in the technical scope of the present invention. Furthermore, it is possible to form novel technical features by combining the technical means disclosed in each of the respective embodiments.

INDUSTRIAL APPLICABILITY

The present invention is applicable in the analysis field of biomolecules, etc.

EXPLANATION OF REFERENCE NUMERALS 1 transfer membrane
1a, 1b end
2 adjuster (transfer-membrane retaining jig)
20 clamp (fixing part, second fixing part, arm part)
21 clamp (fixing part, first fixing part, arm part)
20a, 21a elastic body
20b, 21b pressing member
A abutting part
B shaft
C handle part
20c, 21c stopper (latching member)
20d, 21d anti-slip member
21e lock (latching member)
22 clamp frame (arm part, connection part)
23 carrier (arm part, portion wrapping around upper end of side wall, second portion)
30 anode buffer tank (first buffer solution tank)
31 table
32 anode (first electrode)
33, 34 guide (support member)
40 cathode buffer tank (second buffer solution tank)
41 cathode (second electrode)
42 lock
50 separation unit
50a first opening (dispensing part)
50b second opening
51, 53 insulating plate
52 separation gel (separation medium)
62 motor (drive unit)
63 ball screw (drive unit)
64 guide shaft (drive unit)
65 shaft holder (drive unit)
66 guide pole (arm part, first portion)
68 control unit
100 separation-transfer device

The invention claimed is:

1. A transfer-membrane retaining jig for retaining a transfer membrane in a separation-transfer device that separates analyte by way of electrophoresis, dispenses the analyte thus separated from a dispensing part, and transfers the analyte thus separated to the transfer membrane by causing the transfer membrane to abut the dispensing part and move along a predetermined direction, the transfer-membrane retaining jig comprising:
    a fixing part that fixes at least one end of the transfer membrane in the predetermined direction,
    wherein the fixing part includes: an elastic body that abuts the transfer membrane from an opposite side to the dispensing part; and
    a pressing member that presses the transfer membrane against the elastic body.

2. The transfer-membrane retaining jig according to claim 1, wherein the pressing member undergoes rotation about a shaft that is orthogonal to the predetermined direction and spaced from the transfer membrane to an opposite side to the elastic body, and includes an abutting part that presses the transfer membrane against the elastic body by abutting the transfer membrane, accompanying the rotation.

3. The transfer-membrane retaining jig according to claim 2, wherein the pressing member further includes a handle part operated for the rotation.

4. The transfer-membrane retaining jig according to claim 3, wherein the pressing member has an L-shaped form with the shaft as a corner part.

5. The transfer-membrane retaining jig according to claim 2, wherein the at least one end comprises a first end and a second end, the fixing part further comprises a first fixing part that fixes the first end of the transfer membrane in the predetermined direction,
    wherein a pressing member of the first fixing part comes to press the transfer membrane against the elastic body by rotating so as to drag the transfer membrane in a direction from the second end of the transfer membrane in the predetermined direction towards the first end of the transfer membrane.

6. The transfer-membrane retaining jig according to claim 5, wherein the first fixing part includes a latching member that defines a range of rotation of the pressing member of the first fixing part.

7. The transfer-membrane retaining jig according to claim 5, wherein the fixing part further comprises a second fixing part that fixes the second end of the transfer membrane in the predetermined direction, wherein a pressing member of the second fixing part comes to press the transfer membrane against the elastic body by rotating so as to drag the transfer membrane in a direction from the second end of the transfer membrane towards the first end of the transfer membrane.

8. The transfer-membrane retaining jig according to claim 7, wherein the second fixing part includes a latching member that defines a range of rotation of the pressing member of the second fixing part.

9. The transfer-membrane retaining jig according to claim 2, wherein an anti-slip member is provided to the abutting part.

10. The transfer-membrane retaining jig according to claim 9, wherein the anti-slip member is embedded in the abutting part.

11. A separation-transfer device that separates analyte by way of electrophoresis, dispenses the analyte thus separated from a dispensing part, and transfers the analyte thus separated to a transfer membrane by causing the transfer membrane to abut the dispensing part and move along a predetermined direction, the separation-transfer device comprising:

a transfer-membrane retaining jig for retaining the transfer membrane in the separation-transfer device, wherein the transfer-membrane retaining jig comprising:

a fixing part that fixes at least one end of the transfer membrane in the predetermined direction, wherein the fixing part includes: an elastic body that abuts the transfer membrane from an opposite side to the dispensing part; and a pressing member that presses the transfer membrane against the elastic body.

* * * * *